United States Patent
Badylak et al.

(10) Patent No.: US 6,918,396 B1
(45) Date of Patent: Jul. 19, 2005

(54) METHOD FOR VOCAL CORD RECONSTRUCTION

(75) Inventors: Stephen F. Badylak, West Lafayette, IN (US); Alan R. Spievack, Cambridge, MA (US)

(73) Assignees: Purdue Research Foundation, West Lafayette, IN (US); Clarian Health Partners, Inc., Indianapolis, IN (US)

( * ) Notice: Subject to any disclaimer, the term of this patent is extended or adjusted under 35 U.S.C. 154(b) by 0 days.

(21) Appl. No.: 09/857,307

(22) PCT Filed: Dec. 1, 1999

(86) PCT No.: PCT/US99/28300

§ 371 (c)(1),
(2), (4) Date: May 31, 2001

(87) PCT Pub. No.: WO00/32254

PCT Pub. Date: Jun. 8, 2000

Related U.S. Application Data

(60) Provisional application No. 60/110,401, filed on Dec. 1, 1998, and provisional application No. 60/110,465, filed on Dec. 1, 1998.

(51) Int. Cl.⁷ .......................... A61B 19/00; A61K 35/12
(52) U.S. Cl. ....................................... 128/898; 424/572
(58) Field of Search ................................ 424/572, 423, 424/93.7; 128/898

(56) References Cited

U.S. PATENT DOCUMENTS

| | | | |
|---|---|---|---|
| 4,902,508 A | | 2/1990 | Badylak et al. |
| 5,041,138 A | * | 8/1991 | Vacanti et al. ............... 424/422 |
| 5,372,821 A | | 12/1994 | Badylak et al. |
| 5,445,833 A | | 8/1995 | Badylak et al. |
| 5,516,533 A | | 5/1996 | Badylak et al. |
| 5,549,673 A | | 8/1996 | Beale |
| 5,554,389 A | | 9/1996 | Badylak et al. |
| 5,573,784 A | | 11/1996 | Badylak et al. |
| 5,641,518 A | | 6/1997 | Badylak et al. |
| 5,645,860 A | | 7/1997 | Knapp, Jr. et al. |
| 5,711,969 A | | 1/1998 | Patel et al. |
| 5,755,791 A | | 5/1998 | Whitson et al. |
| 5,762,966 A | | 6/1998 | Knapp, Jr. et al. |
| 5,885,619 A | | 3/1999 | Patel et al. |
| 6,087,157 A | | 7/2000 | Badylak et al. |
| 6,096,347 A | | 8/2000 | Geddes et al. |
| 6,099,567 A | | 8/2000 | Badylak et al. |
| 6,126,686 A | | 10/2000 | Badylak et al. |
| 6,485,723 B1 | * | 11/2002 | Badylak et al. ............ 424/93.7 |

FOREIGN PATENT DOCUMENTS

| | | |
|---|---|---|
| WO | WO 96/40175 | 12/1996 |
| WO | WO 98/10775 | 3/1998 |
| WO | WO 98/25637 | 6/1998 |
| WO | WO 98/40027 | 9/1998 |

OTHER PUBLICATIONS

Landsberg et al., The use of gingival autografts that contain submucosa in the repair of mucogingival defectsin maxillary molars: case reports, Quintessence International, vol. 24 pp. 693–700 (1993).*

Wexler et al., Phonsurgical studies: fat-graft reconstruction of injured canine vocal cords, Ann. of Otology, Rhinolgoy, and Laryngology, vol. 98 pp. 668–673 (1989).*

Isshiki, N. et al., Surgical Treatment of Laryngeal Web with Mucosa Graft, Ann. of Otology, Rhinology, and Laryngology, vol. 100, pp. 95–100 (1991).

Pankratov, M. et al., Endoscopic Diode–laser Applications in Airway Surgery, Proc. SPIE Int. Soc. Opt. Eng., vol. 2128, pp. 33–40 (1994).

Landsberg et al., The use of gingival autografts that contain submucosa in the repair of mucogingival defects in maxillary molars: case reports, Quintessence International, vol. 24 pp. 693–700 (1993).

* cited by examiner

*Primary Examiner*—Justine R. Yu
*Assistant Examiner*—Fenn C. Mathew
(74) *Attorney, Agent, or Firm*—Barnes & Thornburg LLP

(57) ABSTRACT

A method for surgical repair of damaged or diseased head and neck tissues is described. In one aspect of the invention tissue graft constructs comprising vertebrate submucosa or vertebrate basement membrane materials are used to repair and promote growth of endogenous vocal cord tissue.

16 Claims, No Drawings

METHOD FOR VOCAL CORD RECONSTRUCTION

CROSS-REFERENCES TO RELATED APPLICATIONS

This application is a U.S. national application of international application Ser. No. PCT/US99/28300 filed Dec. 1, 1999, which claims priority to U.S. provisional applications Ser. No. 60/110,401 and 60/110,465 filed Dec. 1, 1998.

FIELD OF THE INVENTION

The present invention relates to a tissue graft and method for repairing damaged or diseased head and neck soft tissues. More particularly, this invention is directed to a method for promoting growth of endogenous vocal cord tissue to repair damaged or diseased vocal cords.

BACKGROUND AND SUMMARY OF THE INVENTION

There is a significant need for suitable scaffold materials in reconstructive surgery of the head and neck region. Congenital and acquired deformations of structures such as larynx, soft and hard palate, nasal, auricular, and facial bones are common, and biomaterials available for surgical repair of these objects are limited. Contracture, infection, and poor integration into the surrounding tissues are frequent problems with such materials. Clearly a tissue graft material is desired which is non-immunogenic, is not subject to gross shrinkage after implantation, and promotes the growth of endogenous vocal cord, larynx, soft and hard palate, nasal, and auricular tissues.

The naturally-occurring extracellular matrix (ECM) of the small intestinal submucosa, as well as other vertebrate sources of submucosa, has been shown to serve as a resorbable scaffold for numerous body systems. Surprisingly, it too has been found that basement membranes (stroma) prepared from liver tissue of warm-blooded vertebrates (by removing cellular components of the liver tissue) exhibit mechanical and biotropic properties suitable for use as a tissue graft material. The present invention is directed to the use of vertebrate submucosa matrices and basement membranes as tissue grafts for replacing damaged or diseased portions of head and neck soft tissue and promoting the remodeling and regeneration of the tissue graft with endogenous tissues. The submucosa matrices used in accordance with the present invention comprises highly conserved collagens, glycoproteins, proteoglycans, and glycosaminoglycans in their natural configuration and natural concentration. Vertebrate submucosa is a relatively acellular collagen-based matrix that can be isolated from animal tissues, including particularly intestinal tissue harvested from animals raised for meat production. The isolated submucosa can be used to prepare a resorbable tissue graft construct for inducing the repair of endogenous tissues.

The basement membrane graft compositions of the present invention comprise the basement membrane of organ tissue of a warm-blooded vertebrate, for example, liver tissue, substantially free, preferably devoid, of all cells (e.g., hepatocytes and bile ductal cells) of said warm-blooded vertebrate. The liver basement membrane can be implanted, or fluidized and injected, into a vertebrate host to contact damaged or defective vocal cord, larynx, soft and hard palate nasal and auricular tissues and induce the repair or replacement of said tissues in vivo.

It is known that compositions comprising the tunica submucosa and the basilar portions of the tunica mucosa of the intestine of warm-blooded vertebrates can be used as tissue graft materials in sheet form. See U.S. Pat. No. 4,902,508. The compositions described and claimed in that patent are characterized by excellent mechanical properties, including high compliance, a high burst pressure point, and an effective porosity index which allows such compositions to be used beneficially for vascular graft constructs. The graft materials disclosed in that patent are also useful in tendon, ligament and other connective tissue replacement applications. Furthermore, intestinal submucosa has been used as a scaffold for regenerating other tissues including urinary bladder and dura mater. When used in such applications the preferred graft constructs appear to serve as a matrix for the regrowth of the tissues replaced by the graft constructs. Vertebrate submucosa is a plentiful by-product of commercial meat production operations and is thus a low cost tissue graft material, especially when the submucosa is used in its native sheet configuration. Intestinal submucosa has undergone extensive immunologic testing in over 600 cross-species implants and has never been shown to elucidate a rejection reaction.

Furthermore, it is known that intestinal submucosa can be fluidized by comminution and/or protease digestion, without loss of its apparent biotropic properties, for use in less invasive methods of administration (e.g., injection or topical) to host tissues in need of repair. See U.S. Pat. No. 5,275,826 the disclosure of which is expressly incorporated herein. Fluidized comminuted intestinal tissue comprising tunica submucosa has previously been successfully used to repair and functionally augment damaged tissues including, for example, urinary bladder sphincter. Common events to tissue remodeling include widespread and rapid neovascularization, proliferation of granulation mesenchymal cells, biodegradation of implanted submucosa, and lack of immune rejection.

The present invention is directed to the use of vertebrate-derived submucosa or basement membrane matrices as a graft for the regeneration and repair of head and neck soft tissues including the larynx, vocal cords, soft and hard palate, attached gingiva, nasal and auricular tissues. Such vertebrate extracellular matrices are inexpensive, nonimmunogenic materials that induce host tissue proliferation, remodeling and regeneration upon implantation. In accordance with one embodiment of the present invention tissue graft constructs comprising submucosa or basement membrane of a warm-blooded vertebrate have been found to promote the growth of endogenous vocal cord tissues including the oral mucosal epithelium, connective tissue and skeletal muscle. The graft constructs of the present invention can be used to repair or reconstruct structures damaged by cancer or resulting from congenital defects. The method comprises replacing the damaged or diseased tissues with the construct which acts as a scaffold for endogenous cell growth and replacement of the graft construct. The scaffold is typically entirely replaced by endogenous tissues in about three to six weeks.

DETAILED DESCRIPTION OF THE INVENTION

There is provided in accordance with the present invention a method and composition for repairing damaged or diseased head and neck soft tissues including the vocal cord, larynx, soft and hard palate, attached gingiva, nasal and auricular tissues. The extracellular matrix graft compositions function as a biotropic/biodegradable scaffold that induces endogenous tissues to invade and replace the graft material with endogenous tissue. After implantation, the constructs are eventually remodeled by the host with tissues having a stratification of cell layers similar to that found in normal endogenous tissues.

One tissue graft construct used in accordance with the present invention is derived from vertebrate submucosa and comprises naturally associated extracellular matrix proteins, glycoproteins and other factors. Suitable submucosa comprises the tunica submucosa delaminated from the tunica muscularis and at least the luminal portion of the tunica mucosa. Preferably, the submucosa comprises intestinal submucosa of a warm-blooded vertebrate, and one particularly preferred source of the submucosa is the small intestine of warm-blooded vertebrates. In accordance with one embodiment of the present invention the submucosa is intestinal submucosa comprising the tunica submucosa and basilar portions of the tunica mucosa including the lamina muscularis mucosa and the stratum compactum which layers are known to vary in thickness and in definition dependent on the source vertebrate species. Submucosa can also be prepared from other organs of vertebrate species, for example, from the urogenital system, including the urinary bladder (see U.S. Pat. Nos. 5,554,389), and other portions of the digestive tract including the stomach (see published PCT application no. WO98/25636). The disclosures of U.S. Pat. Nos. 5,554,389 and published PCT application no. WO98125636 are expressly incorporated herein.

The preparation of vertebrate submucosa for use in accordance with this invention is described in U.S. Pat. Nos. 4,902,508 and 5,554,389. To summarize, submucosa is prepared from vertebrate intestine (or other organ source), preferably harvested from porcine, ovine or bovine species, but not excluding other species, by subjecting the intestinal tissue to abrasion using a longitudinal wiping motion to remove the outer layers, comprising smooth muscle tissues, and the innermost layer, i.e., at least the luminal portion of the tunica mucosa. The submucosa is rinsed with saline and optionally sterilized; it can be stored in a hydrated or dehydrated state. Lyophilized or air dried vertebrate submucosa can be rehydrated and used in accordance with this invention without significant loss of its cell proliferative activity. Native submucosa as a starting material is a relatively acellular collagenous matrix and the process of preparing intestinal submucosa for use as the collagenous matrix component of the present invention produces a collagenous matrix devoid of intact cells. Accordingly the submucosa collagenous matrix prepared in accordance with the present invention is acellular.

It is known that compositions comprising the tunica submucosa of the intestine of warm-blooded vertebrates can be used advantageously as tissue graft materials. See U.S. Pat. Nos. 4,902,508 and 5,281,422, the disclosures of which are expressly incorporated herein by reference. The tissue graft compositions described in those patents are used beneficially for vascular graft and connective tissue graft constructs. When used in such applications the graft constructs appear not only to serve as a matrix for the regrowth of the tissues replaced by the graft constructs, but also promote or induce such regrowth of endogenous tissue. Common events to this remodeling process include widespread and rapid neovascularization, proliferation of granulation mesenchymal cells, biodegradation/resorption of implanted submucosa, and lack of immune rejection.

It is also known that intestinal submucosa can be fluidized by comminuting and/or enzymatic digestion, without loss of its apparent biotropic properties, for use in less invasive methods of administration (e.g., by injection or topical application) to host tissues in need of repair. See U.S. Pat. No. 5,275,826, the disclosure of which is expressly incorporated herein by reference.

In another embodiment of the invention the tissue graft composition comprises liver basement membrane prepared by separating same from the natively associated cellular components of liver tissue of a warm-blooded vertebrate. The preparative techniques described below provide an extracellular matrix composition consisting essentially of liver basement membrane substantially free of any cellular components. These compositions are referred to herein generically as liver basement membrane(s) (LBM). Other organ tissue sources of basement membrane for use in accordance with this invention include spleen, lymph nodes, salivary glands, prostate, pancreas and other secreting glands.

Basement membrane for preparation of the graft compositions used in accordance with this invention is typically prepared from liver tissue harvested from animals raised for meat production, including, for example, pigs, cattle and sheep or other warm-blooded vertebrates. Thus, there is an inexpensive commercial source of liver tissue for use in preparation of the basement membrane derived tissue graft compositions for use in accordance with the present invention. In one embodiment, a composition comprising liver basement membranes is prepared from liver tissue of a warm-blooded vertebrate. This composition is useful in accordance with this invention as a non-immunogenic tissue graft capable of inducing endogenous tissue growth when implanted in warm-blooded vertebrates. In one embodiment, the composition comprises an extracellular matrix consisting essentially of liver basement membrane devoid of endogenous cells associated with the source vertebrate liver tissue used to prepared the composition.

The preparation of liver basement membrane from liver tissue of a warm-blooded vertebrate is carried out by removing the cellular components from liver tissue. Ideally the process is carried out to separate the cells from the basement membranes without damaging, or at least minimizing disruption or damage to, the basement membrane tissue. Removal of the cellular components from the liver extracellular matrix allows the preparation of a graft composition that is non-immunogenic, and thus does not induce a host immune response when the graft composition is implanted into a host. In general, the method for preparing a tissue graft composition from warm-blooded vertebrate liver tissue comprises the steps of treating the liver tissue with a cell dissociation solution for a period of time sufficient to release the cellular components of the liver tissue from the extracellular components without substantial disruption of the extracellular components, and separating the cellular components from said extracellular components. Typically the cell dissociation solution comprises a chaotropic agent or an enzyme or both.

The first step in preparing liver basement membrane for use in accordance with one embodiment of the present invention comprises slicing a segment of liver tissue into pieces (e.g., strips or sheets) to increase the surface area-to-volume ratio of the liver tissue. In one embodiment the liver tissue is sliced into a series of sheets each having a thickness of about 0.05 to about 1.5 mm, more particularly, about 50 to about 500 microns, and more preferably about 250 to about 300 microns. Freshly harvested liver tissue can be sliced using a standard meat slicer, or the tissue can be frozen and sliced with a cryomicrotone. The thin pieces of liver tissue are then treated with a solution that releases component liver cells from the associated extracellular basement membrane matrix.

The liver tissue can be also treated with a solution comprising an enzyme, for example, a protease, such as trypsin or pepsin. Because of the collagenous structure of the liver basement membrane and the desire to minimize degradation of the membrane structure during cell dissociation, collagen specific enzyme activity should be minimized in the enzyme solutions used in the cell-dissociation step. In addition, the liver tissue is typically also treated with a calcium chelating agent or chaotropic agent such as a mild detergent such as Triton 100. Thus, in one embodiment of this invention liver tissue is treated by suspending slices or strips of the tissue in a cell-dissociation solution containing enzyme(s) and chaotropic agent(s). However, the cell dissociation step can also be conducted using a calcium chelating agent or chaotropic agent in the absence of an enzymatic treatment of the tissue.

In preparative method the cell-dissociation step is carried out by suspending liver tissue slices in an agitated solution containing about 0.05 to about 2%, more typically about 0.1 to about 1% by weight protease, optionally containing a chaotropic agent or a calcium chelating agent in an amount effective to optimize release and separation of cells from the basement membrane without substantial degradation of the membrane matrix.

After contacting the liver tissue with the cell-dissociation solution for a time sufficient to release all cells from the matrix, the resulting liver basement membrane is rinsed one or more times with saline and optionally stored in a frozen hydrated state or a partially dehydrated state until used as described below. The cell-dissociation step may require several treatments with the cell-dissociation solution to release substantially all cells from the basement membrane. In one embodiment liver tissue is treated with a protease solution to remove the component cells, and the resulting extracellular matrix material (basement membrane) is further treated to remove or inhibit any residual enzyme activity. For example, the resulting basement membrane can be heated or treated with one or more protease inhibitors.

Liver basement membrane for use in carrying out this invention can be fluidized (converted to an injectable or powder form) in a manner similar to the preparation of fluidized intestinal submucosa, as described in U.S. Pat. No. 5,275,826 the disclosure of which is expressly incorporated herein by reference.

In accordance with one embodiment of the present invention a multi-layered submucosa or basement membrane construct is formed from multiple sheets/strips of submucosa and/or basement membrane. The method of forming the multi-layered construct comprises the steps of overlapping multiple sheets of submucosa and/or basement membrane and adhering the layers to each other. The individual layers can be fix to one another using standard techniques know to those skilled in the art and including the use of sutures, staples and biocompatible adhesives such as collagen binder pastes. In one embodiment the layers are fused together by compressing the overlapped regions under dehydrating conditions, optionally with the addition of heat.

The individual layers forming the multi-layered construct can be prepared from sheets of submucosa and/or basement membrane, wherein each sheet is cut to the same dimensions. Alternatively each sheet of the multilayered construct may be cut to have different dimensions, and in one embodiment the sheets comprising the multi-layered construct may have the same width and length but may differ in thickness. Typically the sheets of basement membrane will be cut to have a thickness of about 0.05 mm to about 1.5 mm, and more preferably about 0.2 to about 0.5 mm.

In one embodiment of the present invention, a first strip of submucosa or basement membrane can be partially overlapped with a second strip of submucosa or basement membrane and the two strips adhered to one another to form a large area, graft construct as described in U.S. Pat. No. 5,711,969, the disclosure of which is expressly incorporated herein. The process of forming large area graft sheets involves cutting strips of submucosa and overlapping at least a portion of each strip with a portion of an adjacent strip. The overlapped regions are then adhered to one another using techniques known to those skilled in the art. Alternatively, consecutive layers of extracellular matrix material (submucosa and/or basement membrane) can be layered on top of one another so that each layer is entirely covered by the second layer, thus generating a multi-layered construct uniform in thickness throughout the graft construct. In one embodiment the multi-layered constructs are perforated to allow fluids to readily pass through the graft construct and prevent pockets of fluids from accumulating between the layers. The formation of perforated multilayered constructs is described in U.S. Pat. No, 5,755,791, the disclosure of which is expressly incorporated herein.

In one embodiment, the overlapped portions are compressed under dehydrating conditions to fuse the overlapped portions to one another and form a large sheet. In one preferred embodiment, a multi-layered graft construct is prepared without the use of adhesives or chemical pretreatments by compressing at least the overlapped portions of extracellular matrix under conditions that allow dehydration of the material concurrent with the compression of the tissue. To promote dehydration of the compressed material, at least one of the two surfaces compressing the tissue is water permeable. Dehydration can optionally be further enhanced by applying blotting material, heating the material or blowing air across the exterior of the two compressing surfaces.

In one embodiment the method of forming the multi-layered construct comprises layering the strips onto a permeable surface and using a second optionally permeable surface to compress the overlapped portions between the two surfaces. In one embodiment, strips are organized on a mesh in one direction with at least a portion of one strip overlapping with at least a portion of another strip. Once the mesh is covered with one layer of extracellular matrix material a second layer is applied on top of the first layer but at a different angle relative to the first layer. Additional layers can be added to obtain a graft construct having a desired strength or thickness.

After all the strips are placed on the mesh, another mesh is placed on top of the layers and the "mesh-tissue layers-mesh" sandwich is compressed with a load and dried. This process produces a dried large area construct that can be pealed off the mesh.

In one embodiment the graft construct is formed from two or more strips of extracellular matrix material pressed together and dried through the use of vacuum bagging. In that method submucosa or basement membrane is laid out between two perforated, preferably stainless steel, plates. The plates are shaped to define the desired shape, e.g. two concentric cylinders are used to form a multilayered tubular construct. The material is optionally placed on a surface and covered with blotting material to soak up water, and a breather blanket to allow air flow. The resulting "sandwich" of pressure plates and matrix material is then sealed into a nylon bag that has a vacuum port. A vacuum is applied to pull air out of the vacuum bag and the resulting drop in atmospheric pressure compresses the plates against the matrix material and simultaneously, at least partially, dehydrates the material. After 4 to 24 hours of applying a vacuum, the produced sheet is still moist and very flexible. No seams from the layering are visible and the strength of a prototype 8-thickness sheet as determined by ball burst test is approximately 80 pounds. This general procedure can also be used to shape single tissue strips for use in this invention, if "shaping" of such single layer tissue constructs is determined to be necessary or appropriate for particular surgical application.

In one embodiment, during formation of the large area sheets of tissue, pressure is applied to the overlapped portions under dehydrating conditions by compressing the overlapped tissue segments between two surfaces. The two surfaces can be formed from a variety of materials and in any shape, depending on the desired form and specification of the targeted graft construct. Typically the two surfaces are formed as flat plates but they can also include other shapes such as screens, opposed cylinders or rollers and complementary nonplanar surfaces. Each of these surfaces can optionally be heated or perforated. In preferred embodiments at least one of the two surfaces is water permeable. The term water permeable surface as used herein includes surfaces that are water absorbent, microporous or macroporous. Macroporous materials include perforated plates or meshes made of plastic, metal, ceramics or wood.

Alternatively, large area sheets extracellular matrix graft material can be formed from smaller segments of graft material through the use of sutures and/or the use of binder pastes as described in U.S. Pat. No. 3,562,820, the disclosure of which is expressly incorporated herein by reference. The mechanical properties of the large area grafts can be altered by adjusting the number of layers in the sheet, varying the angle of adjacent layers to each other, and varying the load applied to press the component tissue strips into a large area sheet.

The vertebrate submucosa used in the present invention can be conditioned to alter the viscoelastic properties of the submucosa by stretching the material in a longitudinal or lateral direction as described in U.S. Pat. No. 5,275,826, the disclosure of which is expressly incorporated herein by reference. In accordance with one embodiment submucosa delaminated from the tunica muscularis and luminal portion of the tunica mucosa is conditioned to have a strain of no more than 20%. The submucosa is conditioned by stretching, chemically treating, enzymatically treating or exposing the tissue to other environmental factors. In one embodiment the strips of intestinal submucosa tissue are conditioned by stretching in a longitudinal or lateral direction so that the strips of intestinal submucosa tissue have a strain of no more than 20%.

In one embodiment the submucosa is conditioned by stretching the graft material longitudinally to a length longer than the length of the submucosa from which the graft construct was formed. One method of conditioning the tissue by stretching involves application of a given load to the submucosa for three to five cycles. Each cycle consists of applying a load to the graft material for five seconds, followed by a ten second relaxation phase. Three to five cycles produces a stretch-conditioned graft material with reduced strain. The graft material does not immediately return to its original size; it remains in a "stretched" dimension. Optionally, the graft material can be preconditioned by stretching in the lateral dimension.

In one embodiment the submucosa is stretched using 50% of the predicted ultimate load. The "ultimate load" is the maximum load that can be applied to the submucosa without resulting in failure of the tissue (i.e. the break point of the tissue). Ultimate load can be predicted for a given strip of submucosa based on the source and thickness of the material. Accordingly, one method of conditioning the tissue by stretching involves application of 50% of the predicted ultimate load to the submucosa for three to ten cycles. Each cycle consists of applying a load to the graft material for five seconds, followed by a ten second relaxation phase. The resulting conditioned submucosa has a strain of less than 30%, more typically a strain from about 20% to about 28%. In one preferred embodiment conditioned the submucosa has a strain of no more than 20%. The term strain as used herein refers to the maximum amount of tissue elongation before failure of the tissue, when the tissue is stretched under an applied load. It is expressed as a percentage of the length of the tissue before loading. The conditioned submucosal strips can be used to form a graft construct of the present invention or alternatively the graft construct can be conditioned after its formation. For the multi-layered constructs the submucosa can be stretched prior to the formation of the graft construct, during the formation of the construct, or the submucosa can be stretched after formation of the multi-layered construct.

The graft compositions of the present invention can be sterilized using conventional sterilization techniques including glutaraldehyde tanning, formaldehyde tanning at acidic pH, ethylene oxide treatment, propylene oxide treatment, gas plasma sterilization, gamma radiation, electron beam and peracetic acid sterilization. Sterilization techniques which do not adversely affect the mechanical strength, structure, and biotropic properties of the graft constructs are preferred. For instance, strong gamma radiation may cause loss of strength of the sheets. Preferred sterilization techniques include exposing the graft to peracetic acid, 14 Mrads gamma irradiation (more preferably 1–2.5 Mrads of gamma irradiation) or gas plasma sterilization; peracetic acid sterilization is the most preferred sterilization method. Typically, the graft construct is subjected to two or more sterilization processes. After sterilization, for example by chemical treatment, the tissue graft construct may be wrapped in a plastic or foil wrap and sterilized again using electron beam or gamma irradiation sterilization techniques.

There is provided in accordance with the present invention a method and composition for repairing damaged or diseased head and neck soft tissues including the vocal cord, larynx, soft and hard palate, attached gingiva, nasal and auricular tissues. The above described graft compositions function as a biotropic/biodegradable scaffold that induces endogenous tissues to invade and replace the graft material with endogenous tissue. Advantageously the graft constructs induce the proliferation of endogenous cells to form native tissues of the native structure, including an epithelial cell layer, connective tissue and functional muscle.

In accordance with one embodiment of the present invention, vertebrate submucosa or basement membrane material is used as a tissue graft for reconstructing damaged or diseased larynx and vocal cord tissues. In one embodiment a damaged or diseased section of the vocal cord, or even the entire vocal cord, is removed and replaced with a tissue graft construct as described above. The tissue graft induces the growth of endogenous vocal cord tissues, including oral mucosal epithelial cells, and functional skeletal muscles, and thus promotes the repair of the damaged or diseased tissues. The method of repair comprises the steps of surgically removing the damaged or diseased portion and replacing the removed portion with a tissue graft construct comprising submucosa or basement membrane of a warm-blooded vertebrate. Controls indicate that in the absence of the present graft material, severed vocal cords form scar tissue at the wound site and fail to regenerate the severed vocal cord.

In one embodiment submucosa used for the repair of head and neck soft tissues is isolated from intestinal tissue and comprises the tunica submucosa delaminated from both the tunica muscularis and at least the luminal portion of the tunica mucosa. Alternatively, the submucosa can be prepared from urinary bladder or stomach tissues. In accordance with one embodiment the tissue graft construct comprises multiple layers of vertebrate submucosa comprising 2–12 layers of submucosa, more preferably 4–6 layers. The multi-layered construct in one embodiment comprises partially overlapped strips of submucosa and more preferably the tissue graft construct is formed as a multilayered homolaminate (i.e. having the same number of layers throughout the graft) construct. Basement membrane material can be used similarly alone or in combination with submucosa tissue.

In accordance with one embodiment of the present invention, there is provided a method for reconstructing diseased or damaged vocal cord tissues. The method comprises the steps of surgically removing the damaged or diseased vocal cord tissues and replacing the removed tissues with a tissue graft construct comprising an extracellular matrix of a warm-blooded vertebrate. In one embodiment the entire vocal cord is removed and replaced with submucosa tissue or basement membrane tissue or some combination thereof. The graft construct serves as a scaffold for inducing the proliferation and repair of the vertebrate vocal cords. The graft is remodelled within about three to six weeks forming functional skeletal muscle, an oral mucosal epithelial layer and supporting connective tissue. The tissue graft constructs can be implanted into a vertebrate host species to repair a damaged, diseased or otherwise functionally compromised vocal cord. The xenogeneic materials do not elicit any adverse immune response or adverse inflammatory reaction. The scaffolds appear to be rapidly resorbed and replaced by varying amounts of host connective tissues without shrinkage of the graft area or formation of "scar" tissue.

In one embodiment the defective portion of the larynx or vocal cord is surgically removed and replaced with a tissue graft construct comprising submucosa of a warm-blooded vertebrate. Where the submucosa is of intestinal origin it is preferred that the luminal side of the intestinal submucosa is directed toward the larynx lumen. Large portions of the larynx can be removed and replaced with the tissue grafts of the present invention. After implantation, the constructs are eventually remodelled by the host with functional larynx tissues having a stratification of cell layers similar to that found in the normal larynx wall.

It is anticipated that vertebrate submucosa and/or basement membrane is capable of inducing host tissue proliferation, remodeling and regeneration of appropriate tissue structures upon implantation in a number of microenvironments in vivo (e.g. soft tissues of the head and neck, including the larynx, vocal cords, soft and hard palate, attached gingiva, nasal and auricular tissues). In one embodiment of the present invention the tissue replacement capabilities of graft compositions comprising vertebrate submucosa or basement membrane of warm-blooded vertebrates are further enhanced or expanded by seeding the tissue with various cell types, prior to implantation. For example, a submucosa construct may be seeded with mesenchymal cells (stem cells) initially for expansion of the cell population and thereafter for implantation into a host. In accordance with one embodiment the constructs are seeded with epithelial cells before implantation of the graft construct. In accordance with another embodiment epithelial cells are first cultured on one side of the graft construct and then muscle cells are cultured on the opposite side of the graft construct before the graft is implanted.

EXAMPLE 1

Preparation of Intestinal Submucosa

Small intestine submucosa was prepared in accordance with the procedures described in U.S. Pat. No. 4,902,508. Briefly, sections of porcine jejunum were harvested within ten minutes of euthanasia and immediately placed in 0.9% saline solution. These sections were cut into 10 to 20 cm lengths and the mesenteric tissues were removed from the segment of the small intestine. The small intestine was exerted (inside out) and the tunica mucosa mechanically removed. The small intestinal segment was exerted again (i.e. the stratum compactum on the luminal side, as in the original orientation) and the serosa and tunica muscularis were removed from the outer surface. The tissue was rinsed in saline and placed in a 10% neomycin sulfate solution until used as a graft material. Storage time for the graft material ranged from 2 weeks to 3 months. It should be noted that preparation of submucosa is a mechanical process similar to that of sausage casing and involves no enzymatic reaction steps.

EXAMPLE 2

Surgical Repair of Vocal Cords

Materials and Methods: Seven healthy adult female mongrel dogs were subjected to bilateral resection of the vocal folds. One side was repaired with a single thickness sheet of either intestinal submucosa or urinary submucosa both of which are resorbable naturally-occurring scaffolds. The contralateral side in each dog was left unfilled as a control. The dogs were evaluated at time points ranging from three weeks to several months.

Results: At three weeks, there was significant remodeling along the framework of the resorbable scaffolds. Deposition of new extracellular matrix, an abundant vascular component, and a dense infiltration of mononuclear cells existed within the space occupied by the original graft construct. At three weeks, none of the graft constructs could be identified with either routine H&E staining or Masson's Trichrome staining. There was a subtotal epithelialization of the surface of each of these grafts. The contralateral (control) side showed scar tissue formation partially filling the defect. Macroscopic and microscopic results of the longer surviving dogs are in preparation.

EXAMPLE 3

Preparation of Liver Basement Membrane 2 mM EDTA Chaotropic Solution Used in the Experiment

| | |
|---|---|
| 140 mM | NaCl |
| 5 mM | KCl |
| 0.8 mM | $MgSO_4$ |
| 0.4 mM | $KH_2HPO_4$ |
| 2 mM | EDTA |
| 25 mM | $NaHCO_3$ |

Procedure:

Preparation of liver slices:

Liver frozen in −70° C. was sliced with a cryornicrotone to a thickness of about 50 $\mu M$. The slices of liver tissue were then subjected to enzymatic treatment (trypsin) with a chaotropic solution (samples 1 and 2), with enzyme alone (samples 3 and 4), or with a chaotropic solution alone (sample 5), as indicated below.

| Sample # | Treatment |
|---|---|
| 1) | 0.05% Trypsin in 2 mM EDTA solution |
| 2) | 0.1% Trypsin in 2 mM EDTA solution |
| 3) | 0.05% Trypsin in 2 mM PBS |
| 4) | 0.1% Trypsin in 2 mM PBS |
| 5) | 2 mM EDTA solution |

Liver slices were placed in five 50 ml tubes, each of which contained 25 mL of a different buffered enzyme treatment solution. The liver tissue was incubated at 37° C. in water bath with gentle shaking for 1 hour. The liver slices were washed twice with PBS with agitation/shaking for 1 hour at room temperature. The above enzymatic treatment steps were repeated three times.

The wash buffers were collected and spin them down in 2000 rpm for 10 min. The pellet was suspended and an equal amount of trypan blue was added to identify any remaining cells. The material was checked for presence of cells under microscope.

EXAMPLE 4

Mechanical Properties of Isolated Liver Basement Membrane

Porosity of a graft material is typically measured in terms of ml of water passed per $cm^2\ min^{-1}$ at a pressure of 120 mm Hg. The average "porosity index" established for two separate specimens of LBM was 1162. The suture retention strength of LBM is approximately 68 grams. The material appears to be anisotropic, with the suture strength being approximately the same in all directions.

EXAMPLE 5

Surgical Repair of Vocal Cords

Materials and Methods: Seven healthy adult female mongrel dogs were subjected to bilateral resection of the vocal folds. One side was repaired with a single thickness sheet of LBM which is a resorbable naturally-occurring scaffold. The contralateral side in each dog was left unfilled as a control. The dogs were evaluated at time points ranging from three weeks to several months.

Results: At three weeks, there was significant remodeling along the framework of the resorbable scaffolds. Deposition of new extracellular matrix, an abundant vascular component, and a dense infiltration of mononuclear cells existed within the space occupied by the original graft construct. At three weeks, none of the graft constructs could be identified with either routine H&E staining or Masson's Trichrome staining. There was a subtotal epithelialization of the surface of each of these grafts. The contralateral (control) side showed scar tissue formation partially filling the defect. Macroscopic and microscopic results of the longer surviving dogs are in preparation.

What is claimed is:

1. A method for the repair or replacement of vocal cord tissues comprising the steps of:
   removing a damaged or diseased portion of a vocal cord, and
   replacing the removed portion of the vocal cord with a graft construct comprising vertebrate submucosa or basement membrane.

2. The method of claim 1 wherein the graft construct comprises submucosa and the submucosa is selected from the group consisting of intestinal submucosa, urinary bladder submucosa, and stomach submucosa.

3. The method of claim 2 wherein the submucosa is intestinal submucosa.

4. The method of claim 1 wherein the graft construct comprises vertebrate basement membrane.

5. The method of claim 1 wherein the graft construct comprises 2–12 layers of submucosa.

6. The method of claim 1 wherein the graft construct comprises 4–6 layers of submucosa.

7. The method of claim 5 wherein the graft construct is formed as a multilayered homolaminate construct.

8. The method of claim 1 wherein the graft construct comprises a single layer of submucosa.

9. A method for the repair or replacement of damaged or diseased head or neck soft tissues comprising the steps of:
   removing the damaged or diseased portion of the head or neck soft tissues, and
   replacing the removed portion of tissue with a graft construct comprising vertebrate submucosa or intact basement membrane,
   wherein the head or neck soft tissues are selected from the group consisting of vocal cord, larynx, palate, nasal, and auricular tissues.

10. A method for the repair or replacement of damaged or diseased head or neck soft tissues comprising the steps of:
    removing a damaged or diseased portion of the head or neck soft tissues; and
    replacing the removed portion of tissue with a graft construct comprising vertebrate submucosa or intact basement membrane,
    wherein the head or neck soft tissues include a native structure having an epithelial cell layer, connective tissue, and functional muscle.

11. A method for the repair or replacement of damaged or diseased head or neck soft tissues comprising the steps of:
    removing the damaged or diseased portion of the head or neck soft tissues, and
    replacing the removed portion of tissue with a graft construct comprising vertebrate submucosa or basement membrane,
    wherein the head or neck soft tissues are selected from the group consisting of vocal cord, larynx, and palate tissues.

12. A method for the repair or replacement of damaged or diseased head or neck soft tissues comprising the steps of:
    removing the damaged or diseased portion of the head or neck soft tissues, and
    replacing the removed portion of tissue with an acellular graft construct comprising vertebrate submucosa or basement membrane,
    wherein the head or neck soft tissues are selected from the group consisting of vocal cord, larynx, palate, attached gingiva, nasal, and auricular tissues.

13. A method for the repair or replacement of damaged or diseased head or neck soft tissues comprising the steps of:
    removing the damaged or diseased portion of the head or neck soft tissues, and
    replacing the removed portion of tissue with a graft construct comprising an isolated sheet of extracellular matrix tissue,
    wherein the head or neck soft tissues are selected from the group consisting of vocal cord, larynx, palate, attached gingiva, nasal, and auricular tissues.

14. The method of claim 13 wherein the extracellular matrix tissue comprises vertebrate submucosa or basement membrane.

15. The method of claim 14 wherein the extracellular matrix tissue comprises vertebrate submucosa.

16. The method of claim 14 wherein the extracellular matrix tissue comprises basement membrane.

* * * * *